(12) United States Patent
Kim et al.

(10) Patent No.: US 12,150,847 B2
(45) Date of Patent: Nov. 26, 2024

(54) ROLL-TYPE HOOK TAPE FOR PROVIDING DISPOSABLE DIAPER HOOK MEMBER

(71) Applicant: LARK Industries Co., Ltd., Gimcheon-si (KR)

(72) Inventors: Jong Ryep Kim, Daegu (KR); Kwang Su Yeo, Gumi-si (KR); Man Bae Lim, Daegu (KR); Jung In Park, Daegu (KR); Se Cheol Hwang, Gimcheon-si (KR)

(73) Assignee: LARK INDUSTRIES CO., LTD., Gimcheon-si (KR)

( * ) Notice: Subject to any disclaimer, the term of this patent is extended or adjusted under 35 U.S.C. 154(b) by 452 days.

(21) Appl. No.: 17/567,602

(22) Filed: Jan. 3, 2022

(65) Prior Publication Data

US 2022/0395410 A1     Dec. 15, 2022

(30) Foreign Application Priority Data

Jun. 15, 2021  (KR) ........................ 10-2021-0077137

(51) Int. Cl.
| | | |
|---|---|---|
| *A61F 13/62* | (2006.01) | |
| *A61F 13/49* | (2006.01) | |
| *A61F 13/56* | (2006.01) | |
| *C09J 7/21* | (2018.01) | |
| *C09J 7/29* | (2018.01) | |
| *C09J 7/35* | (2018.01) | |

(52) U.S. Cl.
CPC ...... *A61F 13/625* (2013.01); *A61F 13/49007* (2013.01); *A61F 13/5622* (2013.01); *C09J 7/21* (2018.01); *C09J 7/29* (2018.01); *C09J 7/35* (2018.01); *C09J 2301/304* (2020.08)

(58) Field of Classification Search
CPC .............. A61F 13/625; A61F 13/49007; A61F 13/5622; C09J 7/21; C09J 7/29; C09J 7/35; C09J 2301/304
See application file for complete search history.

(56) References Cited

U.S. PATENT DOCUMENTS

| | | | | |
|---|---|---|---|---|
| 6,526,631 B1 * | 3/2003 | Alberg | ................. | A61F 13/622 604/391 |
| 7,736,352 B2 * | 6/2010 | Jackson | ............ | A61F 13/15756 604/389 |

(Continued)

FOREIGN PATENT DOCUMENTS

| | | |
|---|---|---|
| JP | 2018-68721 A | 5/2018 |
| JP | 2019-511320 A | 4/2019 |

(Continued)

OTHER PUBLICATIONS

Office Action dated Aug. 3, 2021, in connection with Korean Patent Application No. 10-2021-0077137, with English machine translation (9 pages).

(Continued)

*Primary Examiner* — Robert Sandy
(74) *Attorney, Agent, or Firm* — Hauptman Ham, LLP

(57) ABSTRACT

The present invention relates to a roll-type hook tape for providing a disposable diaper hook member, which is more stably fastened to a loop member which is a counterpart of the hook member, and greatly contributes to manufacturing and commercialization in the form of a roll.

3 Claims, 10 Drawing Sheets

(56) References Cited

U.S. PATENT DOCUMENTS

| | | | |
|---|---|---|---|
| 8,758,320 B2 * | 6/2014 | Maruhata | A61F 13/625 604/389 |
| 9,700,466 B2 * | 7/2017 | Hauschildt | A61F 13/5616 |
| 11,298,277 B2 * | 4/2022 | Bogaerts | A61F 13/565 |
| 2017/0196739 A1 * | 7/2017 | Von Jakusch | A61F 13/15723 |
| 2019/0117480 A1 | 4/2019 | Bogaerts et al. | |

FOREIGN PATENT DOCUMENTS

| | | |
|---|---|---|
| KR | 1999-014162 A | 2/1999 |
| KR | 10-2006-0003114 A | 1/2006 |
| KR | 20-2009-0003119 U | 4/2009 |
| KR | 10-1562842 B1 | 10/2015 |

OTHER PUBLICATIONS

Office Action dated Oct. 7, 2021, in connection with Korean Patent Application No. 10-2021-0077137, with English machine translation (4 pages).

* cited by examiner

ROLL-TYPE HOOK TAPE FOR PROVIDING DISPOSABLE DIAPER HOOK MEMBER

CROSS-REFERENCE TO RELATED APPLICATION

This application claims priority under 35 U.S.C. § 119 to Korean Patent Application No. 10-2021-0077137, filed on Jun. 15, 2021, in the Korean Intellectual Property Office, the entire contents of which are hereby incorporated by reference.

BACKGROUND OF THE INVENTION

Field of the Invention

The present invention relates to a roll-type hook tape for providing a disposable diaper hook member, which is more stably fastened to a loop member which is a counterpart of the hook member, and greatly contributes to manufacturing and commercialization in the form of a roll.

Background Art

In general, a disposable diaper includes: a diaper body 10 including nonwoven fabric, an absorber, a waterproof film, and a back sheet disposed from the inside as illustrated in FIG. 1; a loop member 20 having a loop disposed on the upper end portion of the front surface of the diaper body 10; and a hook member 30 having hooks at ends of band portions extending from both sides of the diaper body 10 to correspond to the loop member 20.

Therefore, when a baby wears the disposable diaper, the hook member 30 coupled to both sides of the diaper body 10 is pulled to get in close contact with the loop member 20 fixed on the front surface of the diaper body 10, thereby facilitating convenient connection by fastening between the loop and the hooks.

In other words, the loop member and the hook member respectively have a loop (male portion) and a hook (female portion) which correspond to each other and are capable of repeating attachment and detachment, thereby being widely used for various clothes or shoes, and being widely known as "Velcro" which is a brand name.

The hook has an arch shape, a mushroom shape, a hook shape, and the like, and faces the loop to be fastened to the loop. Such mechanical fastening force enables a user to attach and detach the hook member and the loop member intentionally, but prevents the hook member and the loop member from being separated from each other at random, thereby being widely in place of zippers or buttons.

In addition, a hook member used for a disposable diaper has a structure in which a hook is attached to a tough base nonwoven fabric in which a resin film is laminated on a non-woven fabric fiber or to a nonwoven fabric of a double layer, and the hook member is firmly joined and fixed to a band portion extended to both sides of the upper end of the disposable diaper.

For example, the hook is attached to one side of the base nonwoven fabric of the hook member, and diaper fastening portions to be bonded and fixed to the band portions extending to both sides of the upper end of the disposable diaper are disposed at the other side of the base nonwoven fabric of the hook member. In this instance, the diaper fastening portions are firmly fixed to the diaper band portions, in an overlapped state with the diaper band portions, through a fastening method, such as thermal compression, ultrasonic fastening, or a fastening method using hot melt.

Additionally, the hook member used for a disposable diaper is manufactured and commercialized as a "roll-type hook tape" which has a constant width, is made long in a band shape, and is wound like a roll. Disposable diaper manufacturing factories buy the roll-type hook tapes, and use them after cutting them as long as needed, thereby enabling mass automation production of disposable diapers.

However, most of the conventional roll-type hook tapes used to manufacture hook members for disposable diapers are wide single-body hooks. So, the conventional roll-type hook tapes have a limitation in fastening force for an input amount of the hook.

That is, since the fastening force of the hook is concentrated on the edge portion of one side of the hook sing body, even if the hook is wide, the edge portion is applied only to one place, and so, it is impossible to obtain great fastening force proportional to the amount of the applied hook.

In order to improve the fastening force, a hook division structure that a plurality of narrow hooks are arranged on one hook base nonwoven fabric in multiple stages and are spaced apart from one another at regular intervals to improve the fastening force of the hooks by a plurality of edge portions applied to the one hook member has been proposed. However, because the conventional hook division structure has no specifically technical concept except that the plurality of narrow hooks are arranged sparsely to extend the edge portion, the fastening force gets higher due to the plurality of edge portions, but manufacturing costs are increased due to the use of a great deal of hook materials, and there are an unnatural action that the hooks are caught in multiple stages and a discontinuous motion caused when the hooks are removed from the loop.

In addition, in the case of the conventional hook division structure applied to the roll-type hook tape, since a hot melt adhesive applied to the front surface of the base nonwoven fabric between the plurality of divided hooks is greatly exposed to the outside, the front and rear surfaces of the roll are attached to each other when the roll-type hook tape is rolled for commercialization, and it makes commercialization of the roll-type hook tape difficult.

Hereinafter, conventional arts relating to a hook member, which is applied to a disposable diaper, will be described.

Korean Patent Publication No. 1999-014162 discloses a disposable diaper.

The disposable diaper includes: a diaper body 1 having a front surface 10, a rear surface 20, and a crotch portion 30; and a pair of male fastener tapes, wherein at least one part of the outer surface of the front surface is formed of a non-woven fabric 10a serving as a female fastener tape, a pair of the male fastener tapes 50 extend laterally in the opposite directions to each other from the back face 20 and each of the male fastener tapes 50 has a base sheet 51 and a plurality of male fastening elements 52 standing erect on the base sheet 51, and a cover sheet having the same width as the diaper body 1 extends in the longitudinal direction from a front waist portion 12 of the front surface 10 and is foldable on the nonwoven fabric 10a. Alternatively, the disposable diaper includes: a diaper body 1 having a front surface 10, a rear surface 20, a crotch portion 30, and a pair of male fastener tapes, wherein a pair of the male fastener tapes 50 extend laterally in the opposite directions to each other from the back face 20 and each of the male fastener tapes 50 has a base sheet 51 and a plurality of male fastening elements 52 standing erect on the base sheet 51, and a cover sheet having the same width as the diaper body 1 extends in the longitudinal direction from a front waist portion 12 of the front surface 10 and is nonwoven fabric foldable on the outer surface of the front surface 10 and serves as a female fastener tape, male elements of the male fastener tapes 50 stand erect on the front and rear surfaces of the base sheet 51 to be joined with the front surface 10 and the cover sheet 60. Male elements 52 of the male fastener tapes stand erect on any one among the front surface and the rear surface of the base sheet 51, and at least one of the cover sheet 60 and the front surface 10 corresponding to them is nonwoven fabric bondable with the male faster tape 50.

Korean Patent No. 10-1562842 discloses a 'disposable diaper having a leg guard or a separable belt formed from a laminated outer cover'. The disposable diaper includes: (a) a disposable diaper body that is shaped to fit around a crotch region of a person wearing the diaper; and (b) a separate belt to secure the diaper body to the person, wherein the belt includes at least one Velcro-type fastener comprising a plurality of hooks on the inner surface of the belt, the diaper body has an outer coverstock wherein the outer coverstock has fibers that are at least capable of engaging the hooks and capable of retaining the hooks so that the hooks wrap the fibers of the outer coverstock to hold the fibers of the outer coverstock and the belt can be easily positioned together. The belt may be wrapped around the outer surface of the diaper body and attached to the outer surface of the diaper body through hooks that wrap the fibers of the outer coverstock and attached to the belt itself so that the diaper body fits for a baby's body. The fibers of the outer coverstock are engaged with the hooks of the belt so that the diaper body is in a fixed position relative to the belt and one side of the belt is attached to the other side of the belt when the belt is wrapped around the diaper body. The belt includes a plurality of Velcro-type fasteners spaced apart along the length or section of the belt.

Korean Utility Model Publication No. 20-2009-0003119 discloses a hook assembly of a disposable diaper. The hook assembly of a disposable diaper includes: a fastening band for arranging divided hook tapes on a hook tape area; an empty space part arranged between the divided hook tapes of the hook tape area; a plurality of divided hook tapes arranged across the empty space part in the hook tape area; and a hook edge portion increased by arrangement of the divided hook tapes. The divided hook tapes are formed in a rectangular shape, a wave pattern curve, or a pattern having a circle. The divided hook tapes and the fastening band which is a base material of the hook tapes are attached to each other by ultrasonic fastening. The hook and a loop sheet are bonded discontinuously by arrangement of the divided hook tapes.

PATENT LITERATURE

Patent Documents

Patent Document 1: Korean Patent Publication No. 1999-014162 entitled "Disposable diaper"
Patent Document 2: Korean Patent No. 10-1562842 entitled "Disposable diaper having leg guard or separable belt formed from laminated outer cover
Patent Document 3: Korean Utility Model Publication No. 20-2009-0003119 entitled "Hook assembly of disposable diaper"

SUMMARY OF THE INVENTION

Accordingly, the present invention has been made to solve the above-mentioned problems occurring in the prior arts, and it is an object of the present invention to provide a roll-type hook tape for providing a disposable diaper hook member, which can enhance fastening force by an edge action of multiple stages and minimize an unnatural action that the hook member is caught in multiple stages when the hook member is removed from a loop member, since a plurality of hooks divided at regular intervals are disposed on one hook member.

It is another object of the present invention to provide a roll-type hook tape for providing a disposable diaper hook member, which provides sufficient fastening force even though a small amount of hook materials is used, thereby greatly contributing on reduction of manufacturing cost.

It is a further object of the present invention to provide a roll-type hook tape for providing a disposable diaper hook member, which can perfectly prevent the front surface and the rear surface of the roll from being attached to each other due to an exposure of a hot melt adhesive when the hook member is rolled, thereby contributing on commercialization of the roll-type hook tape.

To accomplish the above object, according to the present invention, there is provided a roll-type hook tape for providing a disposable diaper hook member, which is continuously manufactured in a band shape having a thin thickness and a predetermined width to provide a hook member for a disposable diaper, and is wound in a roll shape to be commercialized, and is cut to a predetermined length from the roll when used as a hook member of the disposable diaper, the roll-type hook tape including: a hook base nonwoven fabric of a band shape in which a non-woven fabric and a thermoplastic resin are laminated; and a handle portion formed on the upper end of the front surface of the base non-woven fabric so as to enable a user to hold and detach the hook member with a hand, wherein the hook member has waves and an identification color so that the user can easily hold it with the hand and easily distinguish it from the disposable diaper having a white background. A hot melt adhesive is applied to the entire surface of the front surface of the base non-woven fabric except for the handle portion. Two or more narrow hooks are fixed below the handle portion of the front surface of the hook base non-woven fabric coated with the hot melt adhesive to be spaced apart from one another at a division interval of the minimum unit. The division interval between the two or more narrow hooks is 0.5 mm to 1.9 mm based on the thickness of the narrow hooks which is 0.25 mm to 0.6 mm. A first diaper fastening portion to be attached to one side of a diaper band portion is disposed on the front surface of the hook base nonwoven fabric on which the hot melt adhesive spaced apart from the narrow hooks at a predetermined interval is coated. A wing film having a second diaper fastening portion which is attached to the diaper band portion on the opposite side of the first diaper fastening portion is fixed on the upper side of the first diaper fastening portion. The wing film is a resin film which has a thickness of 0.1 mm or less, a portion of the wing film is fixed on the front surface of the hook base nonwoven fabric on which the hot melt adhesive between the first diaper fastening portion and the narrow hooks is adhered, the rear surface of the second diaper fastening portion is temporarily adhered by the hot melt adhesive after the second diaper fastening portion is folded upwards, and the front surface of the second diaper fastening portion of the wing film is coated with the hot melt adhesive through additional process.

Moreover, the first diaper fastening portion and the second diaper fastening portion which are exposed to the outside in a state in which the hot melt adhesive is coated may stay as they are, or a release sheet which is temporarily adhered and is removable when the hook member is fastened to the diaper band portion may be adhered onto the first and second diaper fastening portions.

Furthermore, release coating is applied to the rear surface of the hook base nonwoven fabric so that the rear surface is not adhered when getting in contact with the hot melt adhesive.

According to the present invention, the roll-type hook tape for providing a disposable diaper hook member can be conveniently used as a hook member required for fastening a disposable diaper by being unrolled from the rolled hook to a predetermined length and being cut as long as needed. Moreover, the roll-type hook tape for providing a disposable diaper hook member can enhance fastening force with the loop member since the one hook member provides an edge action of multiple stages. Furthermore, the roll-type hook tape for providing a disposable diaper hook member can prevent the unnatural action that the hook member is caught in multiple stages since a division interval (L) between two or more divided narrow hooks (H-1) is optimized within a range not to damage continuous actions when a user removes the hook member from the loop member. The roll-type hook tape for providing a disposable diaper hook member can greatly contribute on commercialization of roll-type hook tapes since perfectly preventing the phenomenon that the front surface and the rear surface of the roll are attached to each other by the hot melt adhesive exposed through the division interval (L) between the narrow hooks (H-1) when the hook member is rolled.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Figure 1:
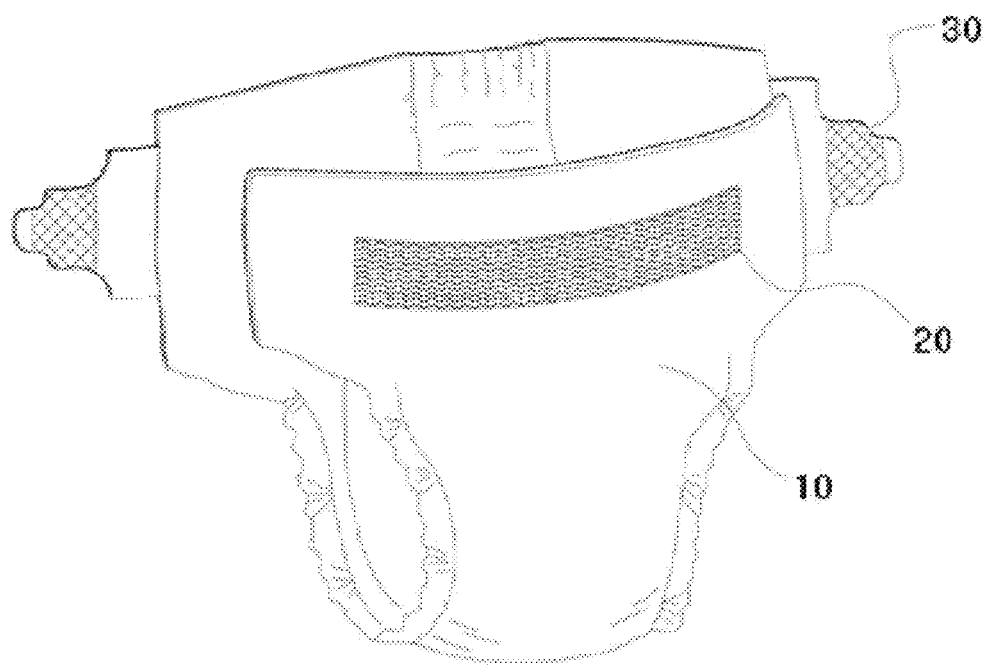
FIG. 1 is a view illustrating a conventional disposable diaper.
Figure 2:
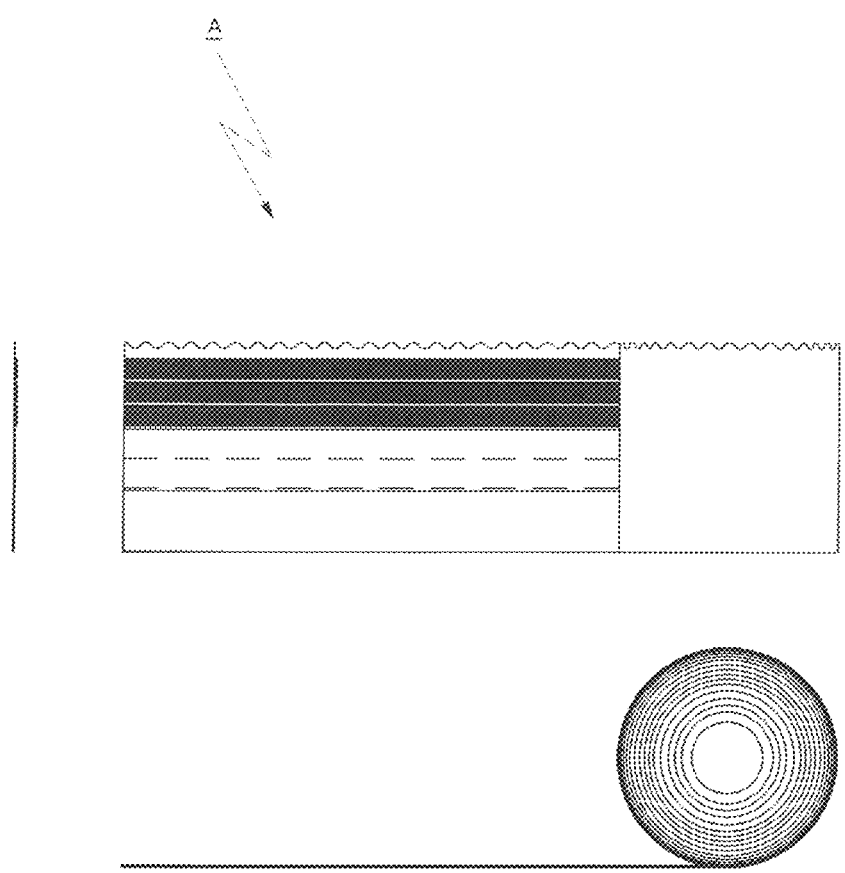
FIG. 2 is a front view, a plan view, and a side sectional view of a roll-type hook tape according to the present invention.
Figure 3:
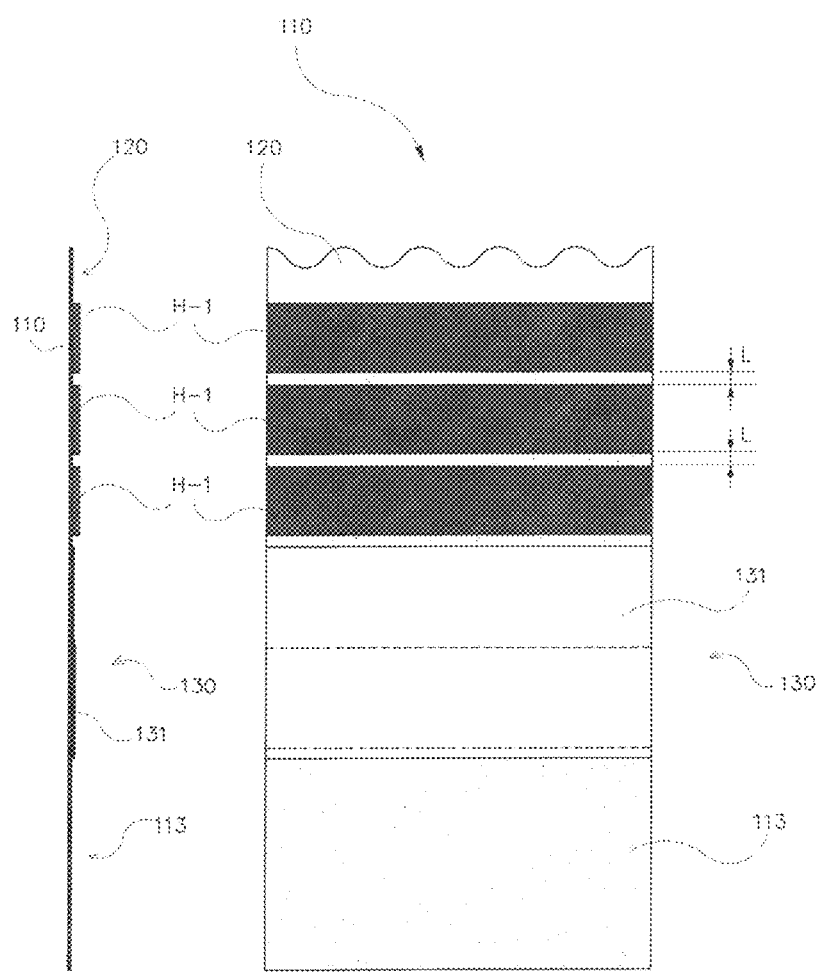
FIG. 3 is a front view and a side sectional view of a hook member which is cut to a predetermined length from the roll-type hook tape according to the present invention.
Figure 4:
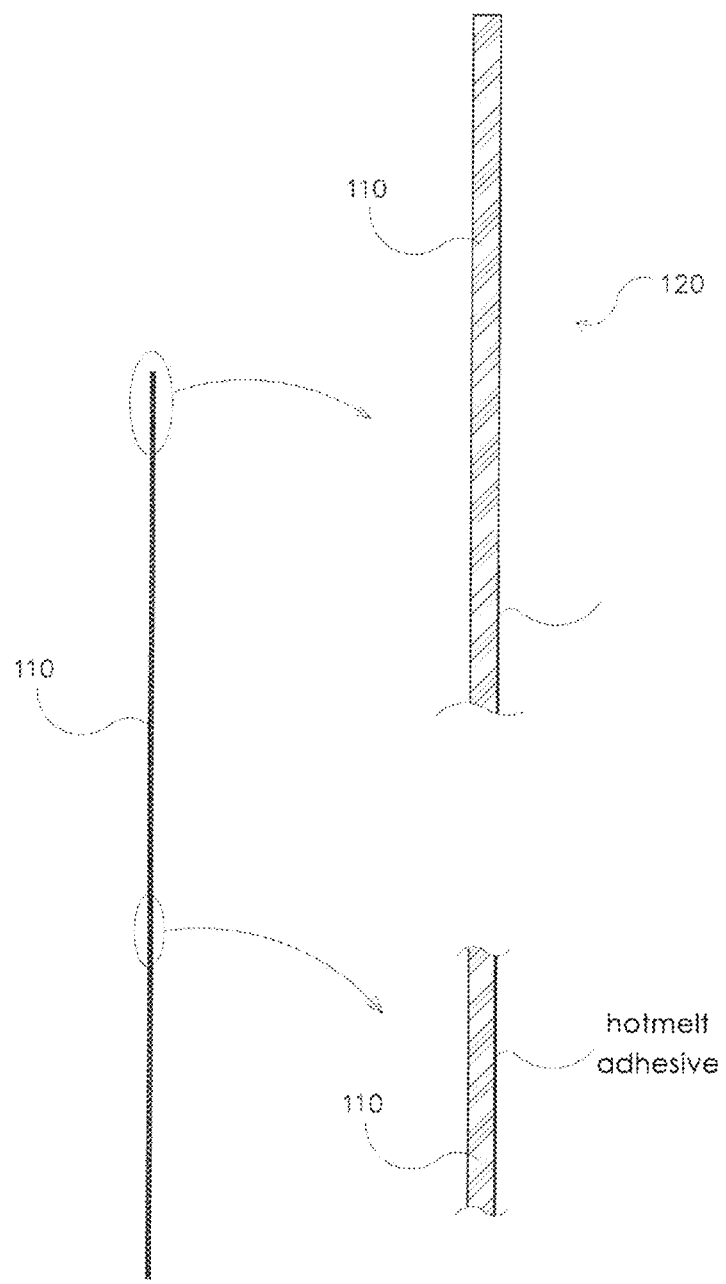
FIG. 4 is a sectional view and a partially enlarged view of a hook base nonwoven fabric 110 according to the present invention.
Figure 5:
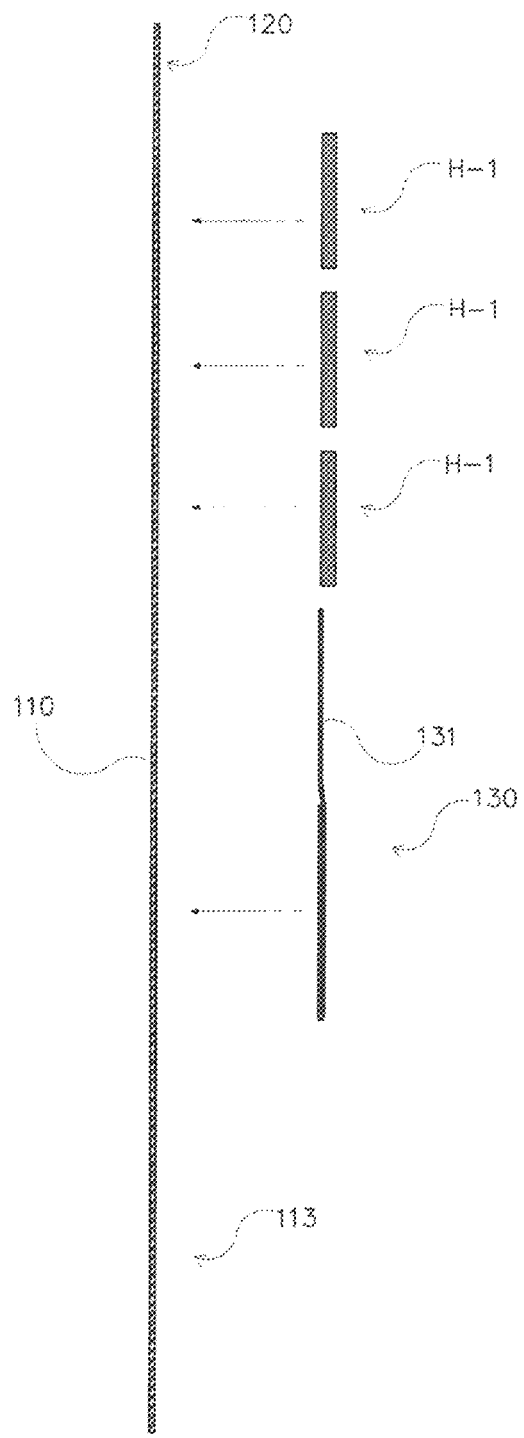
FIG. 5 is a sectional view and partially enlarged view of the hook base nonwoven fabric 110 according to the present invention.
Figure 6:
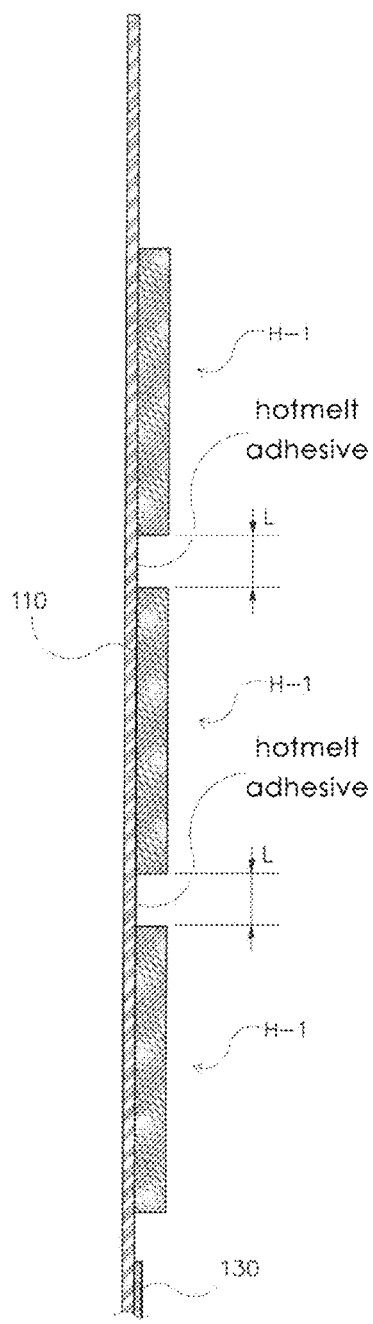
FIG. 6 is a view illustrating a state in which narrow hooks (H-1) and a wing film 130 are adhered.
Figure 7:
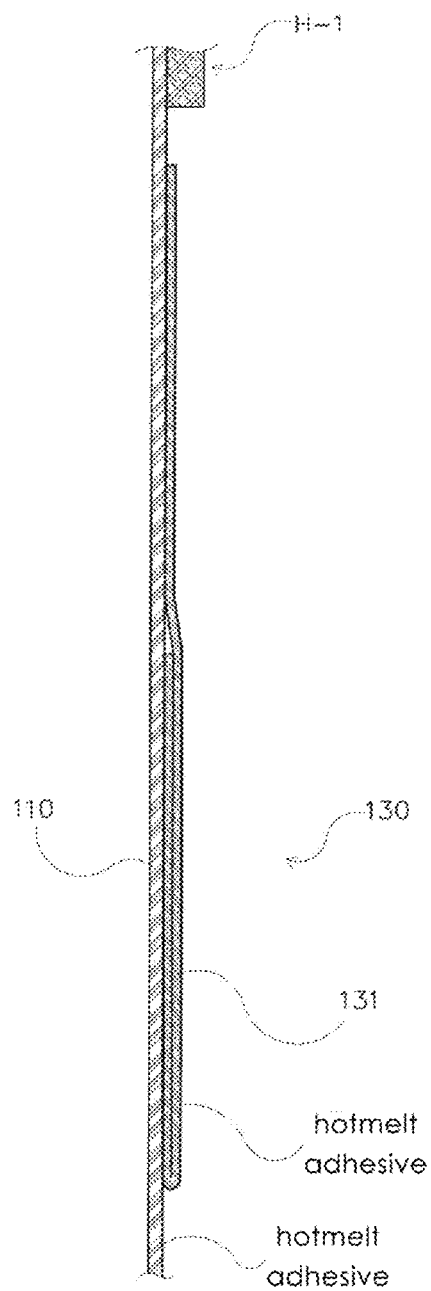
FIGS. 7 to 10 are enlarged sectional views illustrating parts of the hook member according to the present invention.
Figure 8:
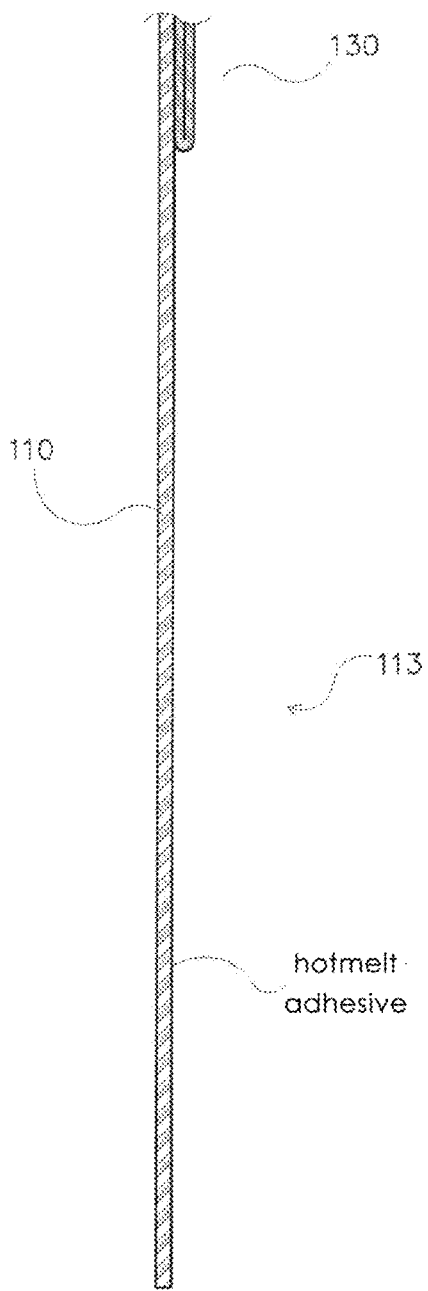
Figure 9:
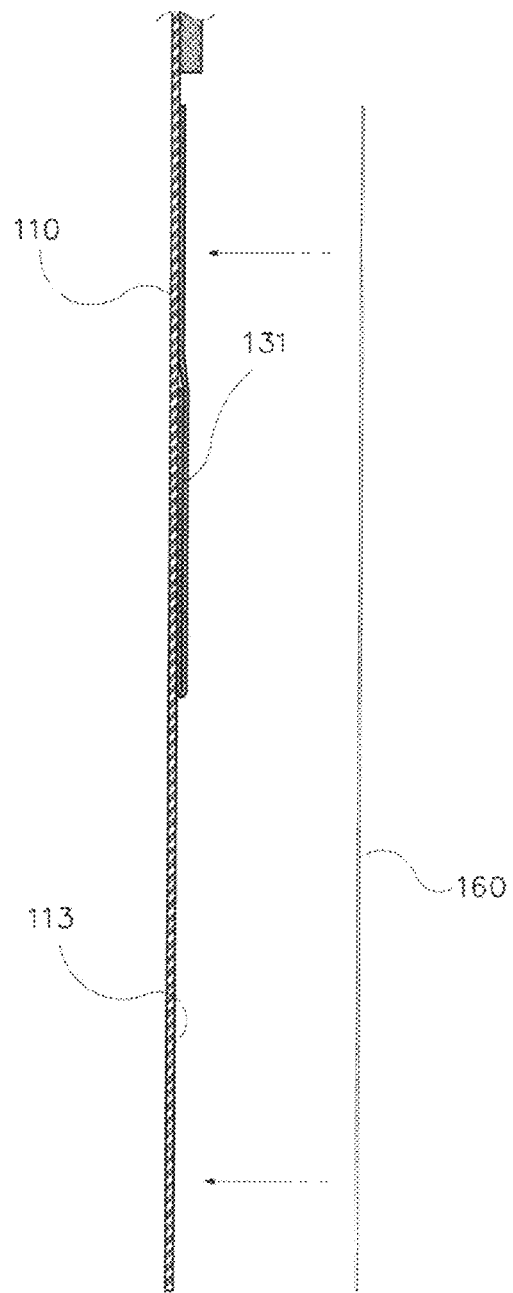
Figure 10:
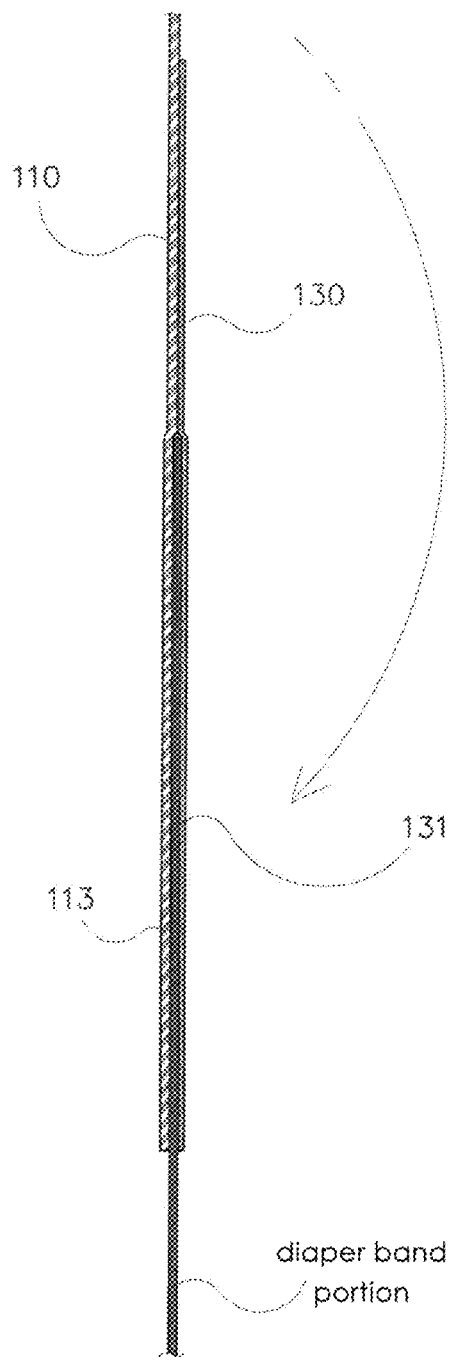

Hereinafter, a roll-type hook tape for providing a disposable diaper hook member according to the present invention will be described in detail with reference to the accompanying drawings.

The present invention relates to a roll-type hook tape for providing a disposable diaper hook member, which is continuously manufactured in a band shape having a thin thickness and a predetermined width to provide a hook member for a disposable diaper, and is wound in a roll shape to be commercialized, and is cut to a predetermined length from the roll when used as a hook member of the disposable diaper.

The roll-type hook tape for providing a disposable diaper hook member according to the present invention includes a hook base nonwoven fabric 110 of a band shape in which a non-woven fabric and a thermoplastic resin are laminated.

Moreover, the roll-type hook tape further includes a handle portion 120 formed on the upper end of the front surface of the base non-woven fabric 110 so as to enable a user to hold and detach the hook member with a hand, wherein the hook member has waves and an identification color so that the user can easily hold it with the hand and easily distinguish it from the disposable diaper having a white background.

Furthermore, a hot melt adhesive is applied to the entire surface of the front surface of the base non-woven fabric 110 except for the handle portion 120.

In addition, two or more narrow hooks (H-1) are fixed below the handle portion 120 of the front surface of the hook base nonwoven fabric 110 coated with the hot melt adhesive to be spaced apart from one another at a division interval (L) of the minimum unit. The division interval (L) between the two or more narrow hooks (H-1) is 0.5 mm to 1.9 mm based on the thickness of the narrow hooks (H-1) which is 0.25 mm to 0.6 mm.

In the meantime, a first diaper fastening portion 113 to be attached to one side of a diaper band portion is disposed on the front surface of the hook base nonwoven fabric 110 on which the hot melt adhesive spaced apart from the narrow hooks (H-1) at a predetermined interval is coated.

A wing film 130 having a second diaper fastening portion 131 which is attached to the diaper band portion on the opposite side of the first diaper fastening portion 113 is fixed on the upper side of the first diaper fastening portion 113.

In this instance, the wing film 130 is a resin film which has a thickness of 0.1 mm or less. A portion of the wing film 130 is fixed on the front surface of the hook base nonwoven fabric 110 on which the hot melt adhesive between the first diaper fastening portion 113 and the narrow hooks (H-1) is adhered. After the second diaper fastening portion 131 is folded upwards, the rear surface of the second diaper fastening portion 131 is temporarily adhered by the hot melt adhesive, and the front surface of the second diaper fastening portion 131 of the wing film is coated with the hot melt adhesive through additional process.

<Disposable Diaper>

In general, a disposable diaper includes: a diaper body 10 including nonwoven fabric, an absorber, a waterproof film, and a back sheet disposed from the inside as illustrated in FIG. 1; a loop member 20 having a loop disposed on the upper end portion of the front surface of the diaper body 10; and a hook member 30 having hooks at ends of band portions extending from both sides of the diaper body 10 to correspond to the loop member 20.

Therefore, when a baby wears the disposable diaper, the hook member 30 coupled to both sides of the diaper body 10 is pulled to get in close contact with the loop member 20 fixed on the front surface of the diaper body 10, thereby facilitating convenient connection by fastening between the loop and the hooks.

<Hook Base Nonwoven Fabric>

The hook base nonwoven fabric 110 is manufactured in a band shape, which is thin and has a predetermined width, using a material in which a non-woven fabric and a thermoplastic resin are laminated in order to solve the problems of strength and toughness when the hook member 30 is used. A handle portion 120 is disposed on the upper end of the front surface of the hook base nonwoven fabric 110 so that the user can hold it with the hand to attach and detach the hook member.

The hot melt adhesive is applied to the entire surface of the front surface of the base non-woven fabric 110 except for the handle portion 120 so as to bond the narrow hooks (H-1) and the wing film 130 and to fasten the diaper.

In this instance, preferably, the handle portion 120 is cut into a wave form and has an identification color, such as blue or red, so that the user can easily hold the handle portion with the hand and the hook member is easily discriminated from the disposable diaper having the white background.

<Narrow Hook>

Two or more narrow hooks (H-1) are fixed below the handle portion 120 of the front surface of the hook base nonwoven fabric 110 coated with the hot melt adhesive to be spaced apart from one another at a division interval (L) of the minimum unit.

Therefore, since lots of narrow hooks are arranged on one hook member of the disposable diaper and the edge action concentrated on an edge of each single hook body is performed in multiple stages, the present invention can enhance fastening force with the loop member, compared with the conventional hook member having an edge at one place.

When the narrow hooks (H-1) are divided into two or more, the division interval (L) between the two or more narrow hooks (H-1) is 0.5 mm to 1.9 mm based on the thickness of the narrow hooks (H-1) which is 0.25 mm to 0.6 mm. Differently from the conventional hook member showing the unnatural action that the divided hooks are caught in multiple stages when the hooks are removed from the loop, the hook member according to the present invention facilitates a continuous one-touch separation action like a undivided single body and is of help to reduce manufacturing costs since using a small amount of hook materials.

Furthermore, if the division interval (L) between the two or more narrow hooks (H-1) is 0.5 mm to 1.9 mm based on the thickness of the narrow hooks (H-1) which is 0.25 mm to 0.6 mm, the hot melt adhesive coated on the entire surface of the hook base nonwoven fabric 110 minimizes exposure to the outside through a gap of the division interval (L) or minimizes an influence on the member corresponding thereto. Especially, the present invention is very useful for commercialization of the roll-type hook tape since preventing the front surface and the rear surface of the roll from attaching to each other when being rolled.

Additionally, the division interval (L) between the two or more narrow hooks (H-1) is limited to the range of 0.5 mm to 1.9 mm. If the division interval is less than 0.5 mm based on the thickness of the narrow hooks (H-1) which is 0.25 mm to 0.6 mm, when the hook member is detached, the narrow hook (H-1) of one side and the narrow hook (H-1) of the other side are bumped against each other, and there is no point in dividing the hooks since the interval is too narrow. If the division interval exceeds 1.9 mm, the hot melt adhesive coated on the hook base nonwoven fabric is exposed to the outside more through the gap in comparison with the thickness of the narrow hooks. So, when the hook member is rolled, the front surface and the rear surface of the roll may be attached to each other. Therefore, the division interval between the two or more narrow hooks must be set to 1.9 mm or less.

<First Diaper Fastening Portion>

The first diaper fastening portion 113 is located below the wing film 130 attached below the narrow hooks (H-1) and is the lowermost portion of the front surface of the hook base nonwoven fabric 110 on which the hot melt adhesive is coated. That is, the first diaper fastening portion 113 is an element adhered on one side of the diaper band portion when the hook member is fixed to the diaper band portion.

<Wing Film>

As illustrated in the drawings, the wing film 130 is a resin film which is less than 0.1 mm thick, and a portion of the wing film 130 is fixed to the front surface of the hook base nonwoven fabric 110 on which the hot melt adhesive is coated between the first diaper fastening portion 113 and the narrow hooks (H-1). The second diaper fastening portion 131 is folded upwards, so that the rear surface of the second diaper fastening portion 131 is temporarily adhered by the hot melt adhesive, namely, the second diaper fastening portion is adhered by the adhesive but is easily removable due to a release treatment.

In this instance, like the front surface of the first diaper fastening portion 113, the front surface of the second diaper fastening portion 131 of the wing film is also coated with the hot melt adhesive through additional process.

In the case of the front surface of the second diaper fastening portion 131 which is coated with the hot melt adhesive and is folded upwards, when the hook member is adhered to the diaper band portion, the folded portion is stretched downwards and is fastened to the opposite side of the diaper band portion to which the first diaper fastening portion 113 is attached, so that the second diaper fastening portion 131 together with the first diaper fastening portion 113 is doubly fastened to the diaper in the form of "Y" so as to provide more firm fastening force.

Moreover, the first diaper fastening portion 113 and the second diaper fastening portion 131 which are exposed to the outside in a state in which the hot melt adhesive is coated may stay as they are, or a release sheet 160 which is temporarily adhered and is removable when the hook member is fastened to the diaper band portion may be adhered onto the first and second diaper fastening portions.

Even though the release sheet 160 is not adhered and the hot melt adhesive is exposed as it is, because the thickness of the two or more narrow hooks (H-1) attached on the wing film 130 is more than twice as thick as the doubly folded wing film 130 and the second diaper fastening portion 131, it is not enough to worry about the phenomenon that the front surface and the rear surface of the hook base nonwoven fabric are attached to each other as pressure caused when the roll-type hook tape is rolled for commercialization is concentrated on the two or more narrow hooks (H-1).

However, because the exposure of the hot melt adhesive may cause a undesirable attachment of the front surface and the rear surface, release coating is applied to the rear surface of the hook base nonwoven fabric 110 which gets in contact with the first diaper fastening portion 113 and the second diaper fastening portion 131 exposed to the outside in the state in which the hot melt adhesive is coated when being rolled, thereby preventing the front surface and the rear surface of the roll from being attached to each other.

What is claimed is:

1. A roll-type hook tape for providing a disposable diaper hook member, which is continuously manufactured in a band shape having a thin thickness and a predetermined width to provide a hook member for a disposable diaper, and is wound in a roll shape to be commercialized, and is cut to a predetermined length from the roll when used as a hook member of the disposable diaper, the roll-type hook tape comprising:

a hook base nonwoven fabric of a band shape in which a non-woven fabric and a thermoplastic resin are laminated; and a handle portion formed on the upper end of a front surface of the base non-woven fabric so as to enable a user to hold and detach the hook member with a hand, wherein the hook member has waves and an identification color so that the user can easily hold it with the hand and easily distinguish it from the disposable diaper having a white background, wherein a hot melt adhesive is applied to the entire surface of the front surface of the base non-woven fabric except for the handle portion, wherein two or more narrow hooks are fixed below the handle portion of the front surface of the hook base nonwoven fabric coated with the hot melt adhesive to be spaced apart from one another at a division interval, and the division interval between the two or more narrow hooks is 0.5 mm to 1.9 mm based on the thickness of the narrow hooks which is 0.25 mm to 0.6 mm, wherein a first diaper fastening portion to be attached to one side of a diaper band portion is disposed on the front surface of the hook base nonwoven fabric on which the hot melt adhesive spaced apart from the narrow hooks at a predetermined interval is coated;

wherein a wing film having a second diaper fastening portion which is attached to the diaper band portion on the opposite side of the first diaper fastening portion is fixed on an upper side of the first diaper fastening portion; and wherein the wing film is a resin film which has a thickness of 0.1 mm or less, a portion of the wing film is fixed on the front surface of the hook base nonwoven fabric on which the hot melt adhesive between the first diaper fastening portion and the narrow hooks is adhered, a rear surface of the second diaper fastening portion is temporarily adhered by the hot melt adhesive after the second diaper fastening portion is folded upwards, and a front surface of the second diaper fastening portion of the wing film is coated with the hot melt adhesive through additional process.

2. The roll-type hook tape according to claim 1, wherein the first diaper fastening portion and the second diaper fastening portion are exposed to the outside in a state in which the hot melt adhesive is coated, or a release sheet which is temporarily adhered and is removable when the hook member is fastened to the diaper band portion is adhered onto the first and second diaper fastening portions.

3. The roll-type hook tape according to claim 1, wherein release coating is applied to a rear surface of the hook base nonwoven fabric so that the rear surface is not adhered when getting in contact with the hot melt adhesive.

* * * * *